United States Patent [19]
Buck et al.

[11] Patent Number: 4,728,433
[45] Date of Patent: Mar. 1, 1988

[54] ULTRAFILTRATION REGULATION BY DIFFERENTIAL WEIGHING

[75] Inventors: Robert J. Buck, Fairfield; John Burbank, Ridgefield; John R. Montgomery, Fairfield, all of Conn.

[73] Assignee: CD Medical, Inc., Miami Lakes, Fla.

[21] Appl. No.: 576,230

[22] Filed: Feb. 2, 1984

[51] Int. Cl.⁴ ............................................. B01D 13/00
[52] U.S. Cl. .................................... 210/646; 210/85; 210/321.3; 210/929; 210/321.71
[58] Field of Search ............... 210/929, 86, 646, 96.2, 210/321.3, 85, 90

[56] References Cited

U.S. PATENT DOCUMENTS

| | | | |
|---|---|---|---|
| 4,132,644 | 1/1979 | Kolberg | 210/929 X |
| 4,178,240 | 12/1979 | Pinkerton | 210/646 |
| 4,204,957 | 5/1980 | Weickhardt | 210/929 X |
| 4,324,663 | 4/1982 | Hirel et al. | 210/929 X |
| 4,582,598 | 4/1986 | Bilstad et al. | 210/433.2 X |

FOREIGN PATENT DOCUMENTS 2397197 3/1978 France ................. 210/929

OTHER PUBLICATIONS

Holmes, et al., "Removal of Fluid from the Patient During Hemodialysis", from *Trans Amer. Soc. for Artif. Int. Organs*, vol. 2, received in PTO 3-17-69, pp. 58-68.

*Primary Examiner*—Frank Spear

[57] ABSTRACT

Hemodialysis ultrafiltration apparatus comprises a hemodialyzer, a supply line for supplying fresh dialysate to the hemodialyzer. A drain line is provided for removing spent dialysate from the hemodialyzer. The dialyzer is adapted to be connected to a patient so that the patient's blood may be supplied to and removed from the hemodialyzer. A weighing mechanism allows a fixed amount of fresh dialysate, by weight, to flow through the hemodialyzer. Spent dialysate emerging from the hemodialyzer is then weighed by the weighing device to determine the weight differential therebetween to monitor and control the amount and rate of ultrafiltrate removed from blood in the hemodialyzer.

A method of hemodialytic ultrafiltration is carried out substantially in accordance with the above-described apparatus.

14 Claims, 1 Drawing Figure

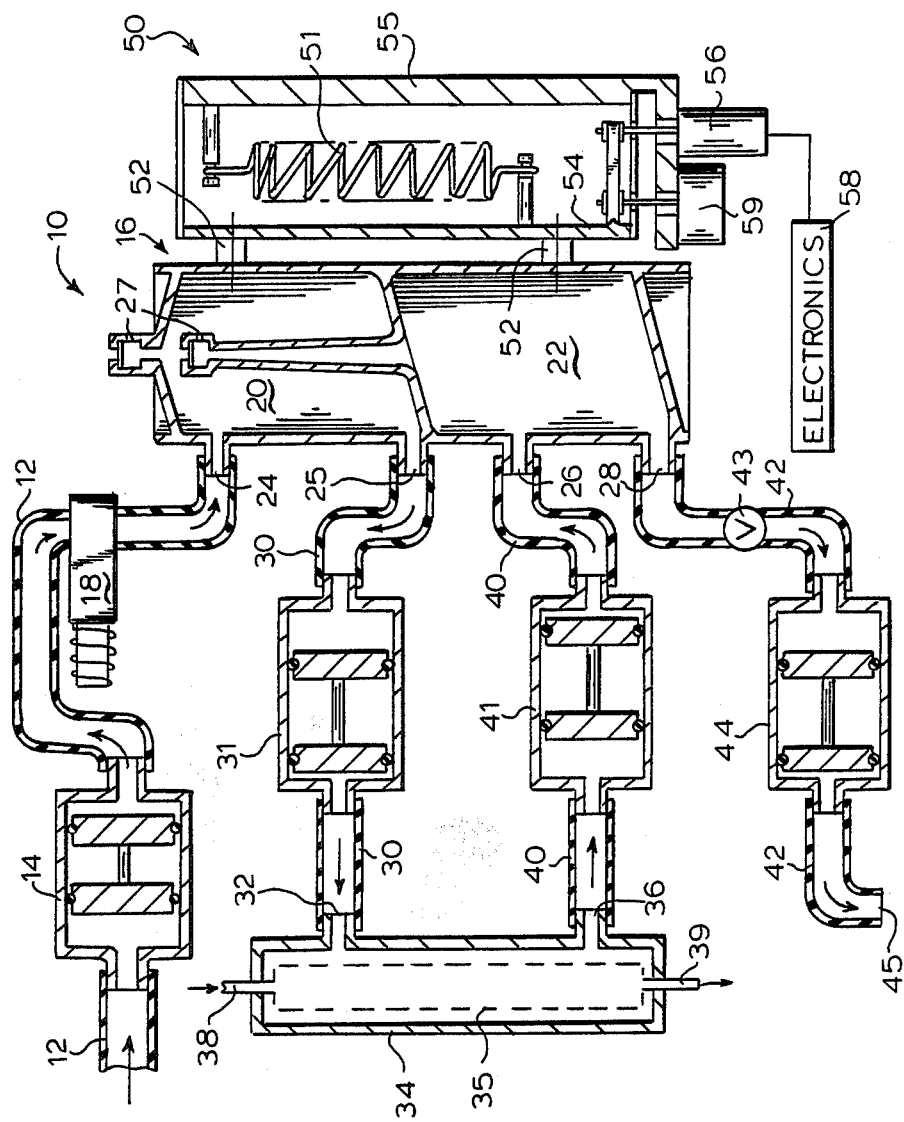

ULTRAFILTRATION REGULATION BY DIFFERENTIAL WEIGHING

BACKGROUND OF THE INVENTION

1. Field of the Invention.

The present invention relates to an ultrafiltration regulation system for hemodialysis purposes, and more particularly, concerns an apparatus and method for regulating ultrafiltration during hemodialysis utilizing volumetric measurement by weight.

2. Description of the Prior Art.

Ultrafiltration is the procedure during hemodialysis wherein excess water is removed from the blood. It is well-known, for example, to achieve satisfactory ultrafiltration by maintaining the dialysate pressure within the dialyser lower than that of the blood pressure. During this procedure, while excess water in the blood is removable, the rate of ultrafiltration is a critical factor, since rapid removal of water from the blood may traumatically affect the patient. Various solutions to the control of the rate of ultrafiltration have been proposed, one of which is found in U.S. Pat. No. 4,021,341.

Other techniques for ultrafiltration regulation include continuously monitoring the weight of the patient during the treatment by means of an in-bed scale. Effective regulation of ultrafiltration, however, has been difficult to achieve using this aforementioned technique.

A different scheme for regulating ultrafiltration by a weighing technique is described in U.S. Pat. No. 4,132,644. This patented approach utilizes a closed liquid container, having a flexible liquid-tight bag within, and a suitable scale for indicating any change in the weight of the content of the container. In use, weight of the inflow of liquid is registered by the scale. After the dialyzing liquid flows through the dialyzer, spent liquid returns to the container. There is a volume of air in the space above the liquid-filled bag, but within the container, which is regulated by a suction pump. This enables a regulated removal of ultrafiltrate from the blood during the dialysis treatment. Since the container is being weighed, the weight of the liquid in the container will increase when ultrafiltrate is added thereto. Thus, the amount of ultrafiltrate can be monitored due to the increase of the total weight in the container. While this patented technique relies upon weight differentials to assess ultrafiltration characteristics, its operation is limited. Specifically, the closed fluid circuit requires a storage container for holding a limited quantity of liquid, which consists of both fresh dialysate and spent dialysate. No provision is made for continuous draining of the spent dialysate, since the container must be opened after the hemodialysis treatment has been completed so that the flexible liquid bag may be removed and then discarded.

Accordingly, improvements in the regulation of ultrafiltration, particularly utilizing volumetric measurement by weight, are still being sought. It is to such an improvement which the present invention is directed.

SUMMARY OF THE INVENTION

The hemodialysis ultrafiltration apparatus of the present invention comprises hemodialysis means. Means supplies fresh dialysate to and removes spent dialysate from the hemodialysis means. Means further supplies and removes blood from the hemodialysis means. Further means allows a fixed amount of fresh dialysate, by weight, to flow through the hemodialysis means and weighs the spent dialysate emerging therefrom. In this fashion, the weight differential between the fixed amount of fresh dialysate and the subsequent spent dialysate is determined to thus monitor and control the amount and rate of ultrafiltrate removed from blood in the hemodialysis means.

In a preferred embodiment of this aspect of the invention, the apparatus for regulating ultrafiltration during hemodialysis includes a hemodialyzer for the dialysis and ultrafiltration of blood. The hemodialyzer includes inlet and outlet blood ports, an inlet dialysate port for the entry of fresh dialysate and an outlet dialysate port for the exit of spent dialysate. A differential weighing receptacle has an inlet chamber and an outlet chamber. This inlet chamber has a fluid inlet opening for receiving fresh dialysate and a fluid outlet opening in fluid communication with the inlet dialysate port of the hemodialyzer for the delivery of fresh dialysate to the hemodialyzer. A fluid inlet opening in the outlet chamber is in fluid communication with the outlet dialysate port of the hemodialyzer for receiving spent dialysate therefrom. A fluid outlet opening in the outlet chamber is provided for the draining of spent dialysate from the outlet chamber. Means concurrently allows the inlet chamber to fill with fresh dialysate while spent dialysate is emptied from the outlet chamber and alternates functions in cyclic fashion. Weighing means is associated with the receptacle for weighing a pre-selected amount of fresh dialysate which fills the inlet chamber when the outlet chamber is substantially empty, and weighs the amount of spent dialysate which fills the outlet chamber when the inlet chamber is substantially empty. The difference in weights between fresh dialysate in the inlet chamber and spent dialysate in the outlet chamber is then determinable to thereby monitor and control the amount and rate of ultrafiltrate removed from blood in the hemodialyzer.

In a further aspect of the present invention, a method of hemodialytic ultrafiltration comprises the steps of suppying fresh dialysate to and removing spent dialysate from hemodialysis means. Blood is supplied to and removed from the hemodialysis means. Further, the method includes allowing a fixed amount of fresh dialysate, by weight, to flow through the hemodialysis means. Spent dialysate associated with the fixed amount of liquid which emerges from the hemodialysis means is then weighed. The method steps include determining the weight differential between the fixed amount of fresh dialysate and the subsequent spent dialysate to monitor and control the amount and rate of ultrafiltrate removed from blood in the hemodialysis means.

In accordance with the principles of the present invention, an ultrafiltration regulation system is provided which utilizes volumetric measurement by weight. In the closed fluid circuit envisioned by the present invention, a true differential in weights of liquid may be determined. Inasmuch as the amount of dialysate is maintained as a constant parameter during the measuring cycle, the additional weight which is detected during the hemodialysis procedure must be attributed to the weight of the ultrafiltrate removed from the blood in the hemodialyzer. By utilizing proper weighing systems and coordinating same with electrical controls, in the preferred embodiment, weight information and data can be accurately and quickly collected, stored and used for a variety of calculations. Accordingly, the amount of ultrafiltrate removed from the blood during each weighing cycle may be calculated; similarly, the ultrafiltration rate for each weighing cycle may be calculated. Moreover, the amount of ultrafiltrate removed from the blood in a specified time period may be regulated by controlling the ultrafiltration rate based on the amount of ultrafiltrate remaining to be removed and the amount of time remaining in the pre-determined dialysis cycle. Very significantly, the present invention provides a mechanism for determining and regulating ultrafiltrate removed from the blood while continuously delivering dialysate to the patient. Although ultrafiltrate measurements are repeated in weighing cycles throughout the dialysis procedure, dialysate flows continuously to the patient on a steady, non-cyclic, basis. Further, spent dialysate is continuously drained from the apparatus of the present invention during the hemodialysis procedure so that no interruptions of dialysis are required to remove or discard spent dialysate as is required in the apparatus of U.S. Pat. No. 4,132,644. The features and elements of the present invention thus monitor and control the amount and rate of ultrafiltrate removed from blood in the hemodialyzer.

BRIEF DESCRIPTION OF THE DRAWING

FIG. 1 is a schematic representation of the major components of the preferred apparatus of the present invention for controlling ultrafiltration during hemodialysis utilizing volumetric measurement by weight.

DETAILED DESCRIPTION

While this invention is satisfied by embodiments in many different forms, there is shown in the drawing and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawing, there is illustrated a schematic representation of the preferred apparatus 10 for controlling ultrafiltration during hemodialysis utilizing volumetric measurement by weight. It is understood that only the major components are represented herein, with minor components being well within the purview of one skilled in the art to ascertain. Water is heated in a heater/heat exchanger (not shown) to a temperature of about 38° C. and is then mixed with dialysate concentrate to form the fresh dialysate supply. Fresh dialysate in line 12 is driven by pump 14 toward a differential weighing receptacle 16. A valve 18 is placed in feed line 12 to regulate the inflow of fresh dialysate into the differential weighing receptacle. Differential weighing receptacle 16 contains two chambers which are isolated from each other: an inlet chamber 20 and an outlet chamber 22. As seen in the figure, inlet chamber 20 is the upper chamber whereas outlet chamber 22 is the lower chamber. Inlet chamber 20 includes two openings, a fluid inlet opening 24 for receiving fresh dialysate, and a fluid outlet opening 25. Similarly, outlet chamber 22 includes two fluid openings, a fluid inlet opening 26 and a fluid outlet opening 28, whose functions shall be described more completely hereinafter. Small air bleeding openings 27 or valves may be included to relieve any air contained in the chambers.

It can be seen in the figure that feed line 12 is connected to fluid inlet opening 24 of the inlet chamber. Another line or fluid conduit 30 is connected to fluid outlet opening 25 of the inlet chamber. Within line 30 is another pump 31, referred to as a pacer pump for control of the dialysate flow rate. Line 30 is connected at its other end to an inlet port 32 of a hemodialyzer 34. Hemodialyzer 34 may be any of the well-known dialyzers useful for hemodialysis which includes a membrane 35 therein adapted to remove waste materials and ultrafiltrate from the blood. Fresh dialysate enters the hemodialyzer through inlet port 32, and after collecting waste materials and ultrafiltrate from the blood, spent dialysate exits the dialyzer through outlet port 36. The hemodialyzer, of course, includes a blood inlet port 38 through which blood from a hemodialysis patient enters; a blood outlet port 39 is provided on the hemodialyzer to return blood, from which waste materials and ultrafiltrate have been removed, to the patient.

Spent dialysate from the hemodialyzer exits outlet port 36 and enters another fluid conduit or line 40. Within line 40 is another pump 41, referred to as a pressure pump for control of dialysate flow to produce the desired rate of ultrafiltration. Line 40 is connected to inlet opening 26 of outlet chamber 22. Fluid in the outlet chamber flows through outlet opening 28 into a fluid line 42 connected thereto, controlled by a valve 43. A drain pump 44 is positioned within line 42 for pumping the spent dialysate out of the outlet chamber of the differential weighing receptacle. Spent dialysate emerges from the opening 45 at the end of line 42 whereupon it may be drained.

As seen in the figure, weighing receptacle 16 is associated with a suspension system 50. This suspension system includes an adjustable tension spring 51 to establish a force to balance the weight of the receptacle. The suspension system, with tension spring, works in the same fashion as well-known weighing scales. Receptacle 16 is mounted within the overall apparatus so as to float whereupon the weight of the receptacle and its contents may be measured (the mounting system is not shown in FIG. 1). Receptacle 16 is connected to suspension system 50 by virtue of flexible bars 52, which are laterally rigid, or framework of the like kind. Included in suspension system 50, and connected to bars 52, is a rigid structural member 54 which is adapted to move vertically depending upon the weight of receptacle 16 and its contents. Another structural member 55, as part of the suspension system, remains in fixed position with respect to the overall apparatus. Since one end of tension spring 51 is connected to movable support member 54 and the other end of the spring is connected to fixed support member 55, tension can be developed in the spring according to the weight of the receptacle. Associated with movable structural member 54 is a transducer 56 for converting the force generated by the weight of the receptacle to an electrical signal so that weight levels are ascertainable electrically. Transducer 56 is preferably a linear variable differential transducer (LVDT) which is amenable to sensing the distance the spring moved, the spring deflection being caused by weight, and then converting the displacement to an electrical signal, in conjunction with the electronics 58. The suspension system also includes a dashpot 59 which serves to damp the movement of structural support member 54 to provide stability to the suspension system. The electronics of the present apparatus, designated by numeral 58 herein, include the electrical controls for operating the ultrafiltration apparatus described herein. Included in the electronics are electrical controls for operating the aforementioned pumps in cyclic fashion in conjunction with the weight sensed by transducer 56, as described above. Further, the electronics include a timing device so that weight measurements may be taken over a specified time period, as will be pointed out hereinafter. In addition, the electronics include well-known devices for displaying information relating to ultrafiltration rate and amounts of ultrafiltrate removed from the blood during the hemodialysis treatment. Controls for removing a specified amount of ultrafiltrate from the blood, in conjunction with pump and valve operation, as well as weight information, are included in the electronics. The details and the elements of the electronics are selectable by the builder of the apparatus described herein, and may include well-known state of the art technology such as microprocessors for achieving the electrical operation of the present apparatus.

Turning now to the operation of ultrafiltration apparatus 10, ultrafiltrate measurements are performed periodically in steps referred to as weighing cycles. For example, the ultrafiltrate measurements may be repeated every thirty seconds; each weighing cycle includes a fill-drain cycle and a fluid transfer cycle, each lasting about fifteen seconds. It is understood, of course, that the time period for the weighing cycle may be varied and is not restricted to the exemplary thirty second weighing cycle herein described. At the beginning of the fill-drain cycle, inlet chamber 20 of the differential weighing receptacle is substantially empty, whereas outlet chamber 22 of the receptacle is either full or contains a substantial amount of spent dialysate. Accordingly, when the fill-drain cycle begins an electrical signal is sent to valve 18 to open this valve to flow of fresh dialysate from the supply. Fresh dialysate is pumped by pump 14 through line 12 through open valve 18 and inlet opening 24 into inlet chamber 20 of the receptacle. Fresh dialysate is continuously being withdrawn from inlet chamber 20 through line 30 regulated by pacer pump 31. This is to assure that dialysate is fed continuously during the hemodialysis procedure through hemodialyzer 34. As alluded to above, pacer pump 31 operates to control the dialysate flow rate. Inasmuch as fresh dialysate is being withdrawn from the inlet chamber, in order to increase the amount of fresh dialysate therein, the rate of inflow delivered by pump 14 must be in excess of the amount being withdrawn by virtue of the operation of pacer pump 31.

While fresh dialysate is being increased within inlet chamber 20, drain pump 44 also commences operation cyclically at the beginning of the fill-drain cycle. Accordingly, the spent dialysate originally inside outlet chamber 22 at the beginning of the fill-drain cycle is emptied therefrom through line 42. In a similar fashion as pacer pump 31, pressure pump 41 also runs continuously so that spent dialysate from hemodialyzer 34 is continuously being delivered through inlet opening 26 to outlet chamber 22. Accordingly, in order to properly drain spent dialysate from the outlet chamber of the receptacle, drain pump 44 must operate at a capacity greater than that of pressure pump 41. Also as alluded to above, pressure pump 41 is controlled by the electronics at a rate sufficient to produce the desired rate of ultrafiltration. At these flow capacities, and for exemplary purposes only, outlet chamber 22 is substantially emptied after about twelve or thirteen seconds of operation, assuming a maximum dialysate flow rate of about 600 ml/minute. With the outlet chamber substantially empty, at the same time the inlet chamber contains a substantial amount of fresh dialysate. After about fifteen seconds of operation in the fill-drain cycle, transducer 56 senses a pre-selected weight established by prior adjustments made in tension spring 51. The weight sensed by the transducer includes not only the weight of the entire differential weighing receptacle, but the amount of fresh dialysate contained within the inlet chamber when the weight measurement is taken. At this moment, there is no spent dialysate being collected in the outlet chamber since whatever spent dialysate is entering is being totally withdrawn through the drain line. Once the pre-selected weight has been sensed by the transducer, the fill-drain cycle has been completed whereupon valve 18 is closed by an electrical signal, and pumps 14 and 44 are temporarily turned off. Upon this occurrence, the fluid transfer cycle commences. With pacer pump 31 and pressure pump 41 being in continuous operation, the pre-determined, fixed amount, by weight, of fresh dialysate in the inlet chamber is withdrawn and passed through hemodialyzer 34. As this fresh dialysate passes through the hemodialyzer, it picks up ultrafiltrate and carries it, along with spent dialysate, by virtue of pump 41 to outlet chamber 22. Accordingly, since ultrafiltrate is added to the dialysate, the total weight of the liquid and the weighing receptacle slowly increases during this fluid transfer cycle. Measurements of ultrafiltration are made only during this fluid transfer cycle since, during the fill-drain cycle no measurements are made even though dialysate fluid continues to be pumped through the hemodialyzer. During the fluid transfer cycle, the weight of the differential weighing receptacle is constantly being monitored by the transducer and the electronics. In this fashion, the difference in weights between fresh dialysate in the inlet chamber and spent dialysate in the outlet chamber is determinable. The rate of weight change may also be determined, which is related to the ultrafiltration weight, and the amount of ultrafiltrate removed during the fluid transfer cycle may also be determined. After a fixed time period in the fluid transfer cycle, normally calculated to prevent running out of fresh dialysate in the inlet chamber, of about fifteen seconds, the fluid transfer cycle terminates and another fill-drain cycle commences. These cycles are alternately repeated so that the regulation of ultrafiltration is continuous. Insofar as differential rates and amounts of dialysate can be distinctly established in accordance with the closed fluid system described above, a number of regulatory and monitoring capabilities are included in the present apparatus. For example, and in conjunction with the electronics herein, the ultrafiltration rate for each weighing cycle may be calculated and displayed to the operator. Further, the amount of ultrafiltrate removed from the blood during each weighing cycle may be calculated and displayed to the operator. Moreover, the present apparatus may be designed to specify a certain amount of ultrafiltrate to be removed from the blood of the patient in a given time period. This is accomplished by continuously controlling the required ultrafiltration rate based on the amount of the ultrafiltrate to be removed from the blood and the amount of time remaining in the pre-determined weighing cycle.

It should be pointed out, that since measurements of ultrafiltration are only taken during the fluid transfer cycle, the ultrafiltration rate is established during the fluid transfer cycle and is extrapolated for the fill-drain cycle. For exemplary purposes, the fill-drain cycle takes about fifteen seconds. At maximum dialysate flow rate of 600 ml per minute, the fluid transfer cycle is also about fifteen seconds. Therefore, the extrapolation for ultrafiltration rate is made at a fifty percent measurement duty cycle. It is evident that as dialysate flow rate is decreased, the measurement duty cycle is increased.

Thus, the present invention provides an apparatus and method for regulating ultrafiltration during hemodialysis utilizing volumetric measurement by weight. The amount and rate of ultrafiltration are determinable by a unique arrangement of components which permits a truly differential weight measurement of fluid inflow verses fluid outflow.

What is claimed is:

1. An apparatus for regulating ultrafiltration during hemodialysis comprising:
   a hemodialyzer for the dialysis and ultrafiltration of blood including inlet and outlet blood ports, an inlet dialysate port for the entry of fresh dialysate and an outlet dialysate port for the exit of spent dialysate including ultrafiltrate added to the dialysate in the hemodialyzer;
   a differential weighing receptacle having an inlet chamber and an outlet chamber, said inlet chamber having a fluid inlet opening for receiving fresh dialysate, and a fluid outlet opening in fluid communication with the inlet dialysate port of said hemodialyzer for the delivery of fresh dialysate to said hemodialyzer, said outlet chamber having a fluid inlet opening in fluid communication with the outlet dialysate port of said hemodialyzer for receiving spent dialysate including any added ultrafiltrate therefrom, and a fluid outlet opening for the draining of dialysate from said outlet chamber;
   means for concurrently allowing the inlet chamber to fill with fresh dialysate while spent dialysate is emptied from the outlet chamber and to alternate functions in cyclic fashion; and
   weighing means associated with said receptacle for weighing a pre-selected amount of fresh dialysate which fills said inlet chamber when said outlet chamber is substantially empty, and for weighing the amount of spent dialysate and ultrafiltrate associated therewith which fills said outlet chamber when said inlet chamber is substantially empty for determining the difference in weights between fresh dialysate weighed in the inlet chamber and spent dialysate, including ultrafiltrate, weighed in the outlet chamber to thereby monitor and control the amount and rate of ultrafiltrate removed from blood in said hemodialyzer.

2. The apparatus of claim 1 wherein said weighing means includes an adjustable tension spring for determining the weight of said receptacle at any given time and a transducer for converting the force generated by said weight to an electrical signal so that weight levels are ascertainable electrically.

3. The apparatus of claim 2 wherein said transducer is electrically connected to said means for controlling the filling and emptying of said chambers so that the inlet chamber is allowed to fill with fresh dialysate until a pre-selected weight level is reached while said outlet chamber is substantially empty, and thereafter for a short period of time fresh dialysate flow into said inlet chamber and spent dialysate flow out of said outlet chamber are prevented whereby the weight of said spent dialysate can be determined for the control of ultrafiltration of the blood.

4. The apparatus of claim 1 wherein means for controlling the filling of said chambers includes an operable valve and a pump associated with the fluid inlet opening of said inlet chamber and a drain pump associated with the fluid outlet opening of said outlet chamber.

5. The apparatus of claim 4 which further includes a pacer pump associated with the outlet opening of said inlet chamber for pumping fresh dialysate to said hemodialyzer and a pressure pump associated with the inlet opening of said outlet chamber for pumping spent dialysate from said hemodialyzer, said pacer and said pressure pumps being operable to continuously pump fluid through the hemodialyzer.

6. The apparatus of claim 1 which further includes means for determining and displaying the ultrafiltration rate and the amount of ultrafiltrate removed from the blood during each weighing cycle and for regulating the amount of ultrafiltrate removed from the blood in a specified time by controlling the ultrafiltration rate based on the amount of ultrafiltrate remaining to be removed and the amount of time remaining in the predetermined weighing cycle.

7. Hemodialysis ultrafiltration apparatus comprising:
   hemodialysis means;
   means for supplying fresh dialysate to and for removing spent dialysate, including ultrafiltrate, from said hemodialysis means;
   means for supplying and removing blood from said hemodialysis means; and
   differential weighing receptacle means for allowing a first amount of fresh dialysate, by weight, to flow into said hemodialysis means and for weighing a second amount of spent dialysate flowing out of said hemodialysis means corresponding thereto, said means further comprising means for determining from the weight differential between the first and second amounts of dialysate the amount and rate of ultrafiltrate removed from the blood in said hemodialysis means.

8. A method for regulating ultrafiltration during hemodialysis comprising:
   supplying blood to and removing blood from a hemodialyzer;
   supplying fresh dialysate to an inlet chamber of a differential weighing receptacle and concurrently removing spent dialysate from an outlet chamber of said receptacle;
   weighing said fresh dialysate in said receptacle, and, upon reaching a pre-selected weight level when said outlet chamber is substantially empty, preventing the further flow of fresh dialysate into said inlet chamber;
   allowing only said fixed amount of fresh dialysate, by weight, to flow through said hemodialyzer;
   collecting spent dialysate including ultrafiltrate, emerging from said hemodialyzer into said outlet chamber and weighing it over a time period not greater than the time period for said fixed amount of dialysate to flow through said hemodialyzer;
   determining the weight differential between said fixed amount of fresh dialysate and said spent dialysate to monitor and control the amount and rate of ultrafiltrate removed from blood in the hemodialyzer.

9. The method of claim 8 wherein the dialysate supplying and removing steps are cyclically repeated so that the regulation of ultrafiltration is continuous.

10. The method of claim 8 wherein fresh dialysate is continuously supplied to and spent dialysate is continuously removed from said hemodialyzer during hemodialysis.

11. The method of claim 8 wherein weight differentials are determined only during the time period when spent dialysate emerging from said hemodialyzer, based on said fixed amount of fresh dialysate, is being collected.

12. The method of claim 8 which further includes determining and displaying the ultrafiltration rate and the amount of ultrafiltrate removed from the blood during the weighing period.

13. The method of claim 12 which further includes regulating the amount of ultrafiltrate removed from the blood in a specified time by controlling the ultrafiltration rate based on the amount of ultrafiltrate remaining to be removed and the amount of time remaining in the weighing cycle.

14. A method of hemodialytic ultrafiltration comprising:

supplying fresh dialysate to and removing spent dialysate, including ultrafiltrate, from hemodialysis means;

supplying and removing blood from said hemodialysis means;

periodically allowing a known amount of fresh dialysate, by weight, to flow into said hemodialysis means;

periodically weighing with a differential weighing receptacle means the amount of spent dialysate associated with said known amount which flows out of said hemodialysis means; and determining the weight differential between the known amount of fresh dialysate and the associated amount of spent dialysate so as to allow the amount and rate of ultrafiltrate removed from the blood in said hemodialysis means to be monitored and controlled.

* * * * *